United States Patent [19]

Weinstein et al.

[11] 4,011,390
[45] Mar. 8, 1977

[54] SEMI-SYNTHETIC AMINOCYCLITOL AMINOGLYCOSIDE ANTIBIOTICS AND METHODS FOR THE PREPARATION THEREOF

[75] Inventors: Marvin J. Weinstein, East Brunswick; Peter J. L. Daniels, Cedar Grove; Gerald H. Wagman, East Brunswick; Raymond Testa, Verona, all of N.J.

[73] Assignee: Schering-Plough Corporation, Kenilworth, N.J.

[22] Filed: June 5, 1974

[21] Appl. No.: 476,638

Related U.S. Application Data

[63] Continuation-in-part of Ser. No. 443,052, Feb. 15, 1974, abandoned.

[52] U.S. Cl. .................................. 536/17; 195/96; 424/181; 536/4
[51] Int. Cl.² .......................................... C07H 15/22
[58] Field of Search ................ 260/210 AB, 210 R

[56] References Cited

UNITED STATES PATENTS

| | | | |
|---|---|---|---|
| 3,669,838 | 6/1972 | Shier et al. | 260/210 AB |
| 3,832,286 | 8/1974 | Weinstein et al. | 260/210 AB |
| 3,907,771 | 9/1975 | Weinstein et al. | 260/210 AB |

*Primary Examiner*—Johnnie R. Brown
*Attorney, Agent, or Firm*—Carver C. Joyner; Stephen B. Coan; Raymond McDonald

[57] ABSTRACT

*Micromonospora inyoensis* strain 1550F-1G NRRL 5742 is incapable of producing antibiotics unless an aminocyclitol is added to the fermentation medium. When such a compound is added, mutamicins are produced, said mutamicins being analogs of known aminoglycoside antibiotics differing therefrom with respect to the aminocyclitol subunit.

6 Claims, No Drawings

SEMI-SYNTHETIC AMINOCYCLITOL AMINOGLYCOSIDE ANTIBIOTICS AND METHODS FOR THE PREPARATION THEREOF

This application is a continuation in part of copending application Ser. No. 443,052, filed Feb. 15, 1974 now abandoned.

This invention relates to novel antibiotics, to acid addition salts thereof and to the preparation of the antibiotics by a novel microbiological process. More particularly, this invention relates to a class of antibiotics which are collectively designated mutamicins and which are individually designated mutamicin 1, mutamicin 2, etc.

The mutamicins are elaborated by a mutant strain of Micromonospora inyoensis herein designated Micromonospora inyoensis strain 1550F-1G. This mutant strain is incapable of producing an antibiotic when cultivated under submerged aerobic conditions in an aqueous nutrient medium absent an aminocyclitol, or an acid addition salt thereof. However, when certain of such compounds are added to the fermentation medium, antibiotics (mutamicins) are produced. When 2-deoxystreptamine is added to the fermentation, sisomicin is produced.

PRIOR ART

In U.S. Pat. No. 3,669,838, issued June 13, 1972, Shier, W. T. et al. describe and claim a process whereby mutant strains of known microorganisms produce antibiotics by the addition of aminocyclitols to the fermentation medium. The aminocyclitols added become a subunit of the elaborated antibiotic. Methods for producing mutants are generally known in the art and include such techniques as exposure of the "parent" microorganism to mutagenic agents such as nitrogen mustards, ultraviolet light, gamma radiation or the like. Following the exposure, survivors are selected and new colonies started therefrom. Those having the capacity to perform the process of this invention may be determined by the procedure described in column 2, lines 13-32 of the aforementioned patent.

DESCRIPTION OF THE INVENTION

This invention may be described as a process for producing mutamicins which comprises fermenting Micromonospora inyoensis strain 1550F-1G in an aqueous nutrient medium, adding to the fermentation a compound of the formula:

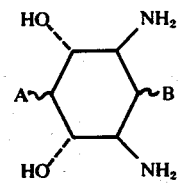

wherein A is a member selected from the group consisting of hydrogen, amino, hydroxy and ($C_1$–$C_8$) alkoxy, B is a member selected from the group consisting of hydrogen and hydroxy, wherein the wavy lines connecting A and B to the ring nucleus denote that such groups may be in any of the possible stereoisomeric forms with the proviso that when B is hydrogen and A is hydroxy, A must be cis to the hydroxy groups adjacent thereto and with the further proviso that when A is amino, it must be trans to the hydroxy groups adjacent thereto; continuing the fermentation until a composition of matter having substantial antibacterial activity is produced and isolating a mutamicin therefrom.

In its composition of matter aspect, this invention may be described as being directed to the aminocyclitol-aminoglycoside antibiotics which are analogs of known compounds of this class differing therefrom with respect to the structure of the aminocyclitol subunit.

This invention is also directed to the use of said novel aminoglycoside antibiotics in the control or destruction of bacterial species, especially which have developed resistance to aminoglycoside antibiotics currently being used.

Sisomicin is an elaborate of unmutated Micromonospora inyoensis and has the chemical name and structure below:

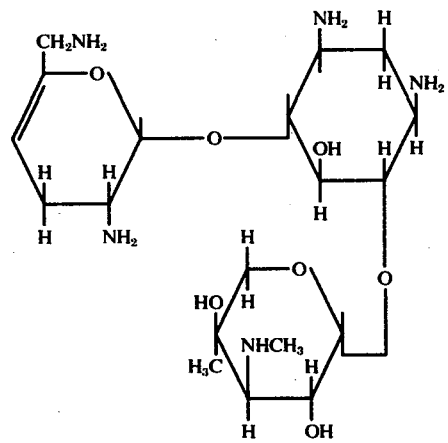

O-2,6-Diamino-2,3,4,6-tetradeoxy-α-D-glycero-hex-4-eno-pryanosyl(1 → 4)-O-[3-deoxy-4-C-methyl-3-(methylamino)-B-L-arabinopyranosyl(1 → 6)] -2-deoxy-D-streptamine.

The moiety in the upper right of Formula I is derived from 2-deoxystreptamine and is the one moiety by which the mutamicins differ from each other and from known aminoglycoside antibiotics.

Aminocyclitols are well known in the field of antibiotic chemistry and are usually saturated carboxylic ring compounds having amino groups and hydroxyl groups attached to the ring. They may also be described as cyclic polyols wherein one or more hydroxyl groups have been replaced by an amino group.

THE MICROORGANISM

The patent microorganism (Micromonospora inyoensis) is described in the Journal of Antibiotics (Japan) Vol. XXIII, No. 11, pages 551–558 (1970) in a publication by M. J. Weinstein, et al.

Micromonospora inyoensis strain 1550F-1G exhibits growth characteristics that are similar to Micromonospora inyoensis (the microorganism from which it is derived). M. inyoensis, the unmutated microorganism, is deposited with U.S. Department of Agriculture, Northern Utilization Research and Development Division, Peoria, Ill., where it was assigned to the numerical designation NRRL 3292. A culture of M. inyoensis strain 1550G-1G has been deposited with the above-mentioned depository where it was assigned the numerical designation NRRL 5742.

The following tables set forth a number of taxonomical, biochemical and morphological properties of the microorganism. In the description of the microorganism, two color designates are used. The first is a color name taken from the "Descriptive Color Name Dictionary" by Taylor, Knoche and Granville published by the Container Corporation of America (1950) USA, with a color chip number corresponding to the color name, the chip number being taken from "The Color Harmony Manual," 4th Edition, 1958 published by the Container Corporation of America. The second designator consists of a color name and number which refers to the synonym or near synonym found in the National Bureau of Standards, Circular 553, Nov. 1, 1955 (USA).

TABLE I

Morphology of Micromonospora inyoensis Strain
1550 F-16 NRRL 5742
Medium: 3% NZ Amine Type A, 1% Dextrose, 1.5% Agar

| Observations | |
|---|---|
| Macroscopic | Microscopic |
| Growth poor, not sufficient for characterization. | |

TABLE II

Colony Description of Micromonospora Inyoensis Strain 1550F-16
NRRL 5742 on Various Media or conditions

| Medium or Condition | Observations |
|---|---|
| Sucrose | Utilized |
| Temperature | Grows well at 28° and 37° C<br>No growth at 50° C |
| Aerobic or Anaerobic | Aerobic |
| Czapeks Medium (Glucose) | Growth, fair to poor, plicate-membranous, no diffusible pigment g3ic light amber - dark orange yellow 72 |
| Asparagine-Glucose Medium | Growth fair to poor, flat to membranous, no diffusible pigment g3ic light amber - dark orange yellow 72 |
| Calcium Malate Agar | Growth poor, flat, no diffusible pigment g3ic light amber - dark orange yellow 72 |
| Nitrate Reduction | Variable |
| Ordinary Agar (Water Agar) | Growth poor, insufficient for description |
| Nutrient Agar | Growth fair to poor, flat to slightly wrinkled g4ne luggage tan - strong brown 55 to g4pn chocolate brown - dark brown 59 |
| Loffler's Serum Medium (Difco) | Growth fair, substrate partially liquefied g5pe terracotta - strong brown 5 |
| Potato Plug | No growth |
| Peptone Glucose Agar | Growth fair to poor, flat to slightly furrowed, no diffusible pigment produced g4ne luggage tan - strong brown 55 |
| Egg Agar (Dorset Egg Medium - Difco) | Growth poor, insufficient for characterization |
| Gelatin Medium | Growth fair to poor, flat to slightly ridged, no diffusible pigment produced, gelatin weakly hydrolyzed g41e turf tan - light brown 57 |
| Starch Agar | Growth fair, flat, no diffusible pigment, starch weakly hydrolyzed only directly under colony g3 1e yellow maple - strong yellowish brown 74 to black |

TABLE II-continued

Colony Description of Micromonospora Inyoensis Strain 1550F-16
NRRL 5742 on Various Media or conditions

| Medium or Condition | Observations |
|---|---|
| Tyrosine Medium | Grow fair to poor, flat, slight darking of medium g41e turf tan - light brown 57 |
| Litmus Milk (Difco) | Peptonized, acid reaction |
| Cellulose Medium | Cellulose poorly decomposed (hydrolysis of cellulose weak) |
| Bennett's Agar | Growth good, membranous - plicate, no diffusible pigment black |
| Emerson's Agar | Growth good, membranous, no diffusible pigment g3ni clove brown, dark yellowish brown 78 |
| Tomato Paste Oatmeal Agar | Growth fair, raised, ridged, no diffusible pigment g4nc russet orange, strong orange 50 |
| Glucose Yeast Extract Agar | Growth good, membranous, no diffusible pigment black |
| Potato Slice | + CaCO$_3$ +++ growth, black<br>− CaCO$_3$ no growth |
| Tyrosine-Agar Yeast Ext. | Growth good, membranous, crystals dissolved, light brown diffusible pigment produced |
| Tyrosine - Beef Extract Growth fair to poor crystals weakly dissolved, brownish diffusible pigment produced only on cross-hatched method | Observations at 2, 7 and 14 days (after Gordon and Smith, J. Bact. 69:147 (1955)) |
| Peptone Iror Agar Observations at 2, 7 and 14 days | No growth, no reaction |

TABLE III

Utilization of Nitrogen Sources by Micromonospora Inyoensis Strain 1550F-G NRRL 5742

| Nitrogen Source +1% glucose | Observations |
|---|---|
| 0.5% Difco Yeast Extract | Growth good, membranous, no diffusible pigment produced black |
| 1.0% NZ Amine Type A | Growth good, membranous, plicate g4nc russet orange, strong orange 50 to black |
| 1% Asparagine | Growth poor, insufficient for description |
| 1% Glutamic Acid | Growth poor, insufficient for description |
| 1% Sodium Nitrate | Growth poor, insufficient for description |
| 1% Ammonium Nitrate | Growth poor, insufficient for description |

TABLE IV

Utilization of Carbohydrates by Micromonospora Inyoengia Strain 1550F-1G NRRL 5742

| | Growth |
|---|---|
| Control | ± poor |
| d-Arabinose | ± poor |
| L-Arabinose | ± poor |
| Dulcitol | ± poor |
| D-Galactose | + fair |
| D-Glucose | ++ good |
| Glycerol | ± poor |
| I-Inositol | ± poor |
| D-Lactose | ± poor |
| D-Levulose | + fair |
| D-Mannitol | ± poor |
| Mannose | +++ good |
| Melibiose | ± poor |
| Melizitose | ± poor |
| Raffinose | ± poor |
| L-Rhamnose | ± poor |
| D-Ribose | + fair |

TABLE IV-continued

Utilization of Carbohydrates by *Micromonospora Inyoengia* Strain 1550F-1G NRRL 5742

| | |
|---|---|
| Salicin | ± poor |
| Sucrose | + fair |
| D-Xylose | ++ good |

THE FERMENTATION

In order to produce the Mutamicins, a lyophilized culture or cells from a slant culture, of *Micromonospora inyoensis* strain 1550F-1G NRRL 5742 is transferred to a sterile inoculum medium. The medium is an aqueous one containing assimilable sources of nitrogen, carbohydrates and the usual compliment of trace metals. The inoculated medium is permitted to incubate under aerobic conditions at from about 24° to about 40° C, preferably about 35° C for from about 2 to about 5, preferably about 3 days. The pH is maintained in the range of from about 6.0 to about 8.0, preferably from about 6.8 to about 7.4.

The so-produced inoculum is aseptically transferred to a fermentation medium, which medium may be the same as or different from the inoculum medium. An aminocyclitol may be added to the fermentation medium before sterilization, at the time of inoculation or up to 48 hours after inoculation. Further, the aminocyclitol which may be in the form of an acid addition salt is usually dissolved in water, sterile filtered and added to the fermentation medium. In general, the concentration of the compound is from about 100 to above 1500 mcg/ml. of fermentation broth. The fermentation is conducted under aerobic conditions, and under about the same conditions of temperature and pH as is the inoculum. Peak antibiotic production is determined by the assay used for sisomicin [see J. Antibiotics (Japan) Vol. XXIII]. The mutamicins are isolated from the fermentation and from co-produced minor components having antibacterial activity by methods generally used in the art for aminoglycoside antibiotics. For example, the acidified broth is separated from the mycelium. After neutralization, the antibiotic is adsorbed from the broth by ion exchange techniques and desorbed from the ion exchange resin yielding an aqueous solution rich in antibiotic. The solution may be lyophilized to yield the antibiotics in solid form, or alternatively, the solution may be subjected to purification techniques, such as chromatography to yield the mutamicin in substantially pure form free from co-produced minor components.

THE ANTIBIOTICS

As stated above, the mutamicins are analogs of known aminoglycoside antibiotics but differ therefrom and from each other with respect to the structure of the aminocyclitol subunit. The major components isolated from the fermentation of *Micromonospora inyoensis* strain-1550f-1G NRRL-5742 are analogs of sisomicin differing therefrom only in the structure of the aminocyclitol subunit. Thus, they may be described as tricyclic aminocyclitol-aminoglycoside antibiotics having the general formula:

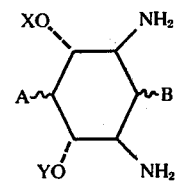

wherein X is 2,6-diamino-2,3,4,6-tetradeoxy-α-D-glycero-hex-4-enopyranose; Y is 3-deoxy-4-c-methyl-3-(methylamino)-β-L-arabinopyranose; A is a member selected from the group consisting of hydrogen, amino, hydroxy and alkoxy ($C_1$–$C_8$); B is a member selected from the group consisting of hydrogen, and hydroxy; and wherein the wavy lines connecting A and B to the ring nucleus denote that such groups may be in any of the possible stereoisomeric forms with the proviso that when B is hydrogen and A is hydroxyl, A must be cis to the glycosyl groups adjacent thereto and with the further proviso that when A is amino, it must be trans to the glycosyl groups adjacent thereto.

Mutamicin 1 is that analog of sisomicin wherein 2-deoxystreptamine is replaced by streptamine and may be represented by formula III below:

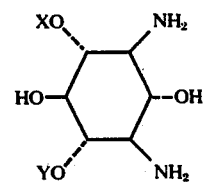

wherein X and Y are as defined above.

Mutamicin 2 is that analog of sisomicin wherein 2-deoxystreptamine is replaced by 2,5-dideoxystreptamine and may be represented by formula IV below:

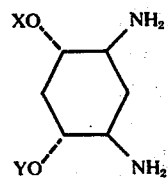

wherein X and Y are as defined above.

The precursor for mutamicin 2 (i.e. 2,5-dideoxystreptamine) is novel and may be prepared by a novel synthesis described in the application of Peter J. L. Daniels and Mohammad Mehdi Nafissi Varchei, entitled, "Process for the Preparation of 2,5-dideoxystreptamine and of a Novel Intermediate Therefor," Ser. No. 443,051, filed Feb. 15, 1974.

Mutamicin 4 is that analog of sisomicin wherein 2-deoxystreptamine is replaced by 2-epistreptamine (myo-inoso-1,3-diamine) and may be represented by formula V below:

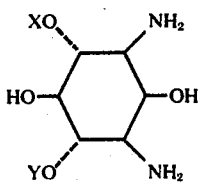

wherein X and Y are as defined above.

Mutamicin 5 is that analog of sisomicin wherein 2-deoxystreptamine is replaced by 1,3,5-triaminocyclohexane-4,6-diol and may be represented by formula VI below:

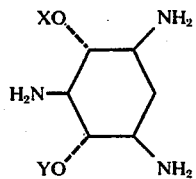

wherein X and Y are as defined above.

Mutamicin 6 is that analog of sisomicin wherein 2-deoxystreptamine is replaced by 5-epi-2-deoxystreptamine and may be represented by formula VII below:

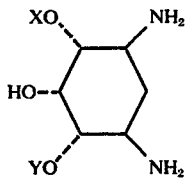

wherein X and Y are as defined above,

The mutamicins readily form non-toxic salts with organic and inorganic acids, such as for example hydrochloric, sulfuric, phosphoric, acetic, stearic, propionic, tartaric, maleic, benzoic, acid and the like. In general, the salts are water soluble and may be obtained by concentration or lyophilization of an aqueous solution thereof or by precipitation with a water miscible organic solvent preferably a lower aliphatic alcohol or ketone.

The mutamicins also form non-toxic Schiff baseoxazolidine derivatives when reacted with aldehydes under standard reaction conditions. Exemplary of the aldehydes whose use is contemplated are acetaldehyde, propionaldehyde, butraldehyde, crotonaldehyde furfural, cyclopentylacetaldehyde, vanillin, veratraldehyde, benzaldehyde, p-nitrobenzaldehyde, salicylaldehyde, pyridoxal and the like. These condensation products are not appreciably soluble in water but are soluble in most commonly used organic solvents such as chloroform, methanol, acetone, ethyl acetate and the like.

PREPARATION OF PRECURSORS

The compounds which are utilized by *Micromonospora inyoensis* strain 1550F-1G NRRL 5742 to produce the mutamicins are generally obtained from one of two sources. The first is by the hydrolysis of known antibiotics followed by separation, isolation and recovery of the aminocyclitol sub-unit. Exemplary of the compounds obtained in this manner are streptamine and 2-deoxystreptamine the last named compound being obtained from the hydrolysis of gentamicin or kanamycin. The preparation of streptamine by the stepwise hydrolysis of streptomycin is described by Fried, J. Et al. in the J. Biological Chemistry, 162, 381 (1946).

The second source by which the intermediate compounds are obtained is by chemical synthesis from readily available starting materials. Included in this group is the aminocyclitol of mutamicin 2,(2,5-dideoxystreptamine) which may be prepared by treatment of the dicarbamate of 2-deoxystreptamine (VIII) with iodomethyltriphenylphosphorane to form the 5-iodo derivative (IX). The iodo group is removed via hydrogenolysis to yield the 2,5dideoxystreptamine carbamate which compound in the presence of aqueous acid yield 2,5-dideoxystreptamine (X) as an acid addition salt.

The free amine is generated in the usual manner (e.g. by treatment with aqueous alkali).

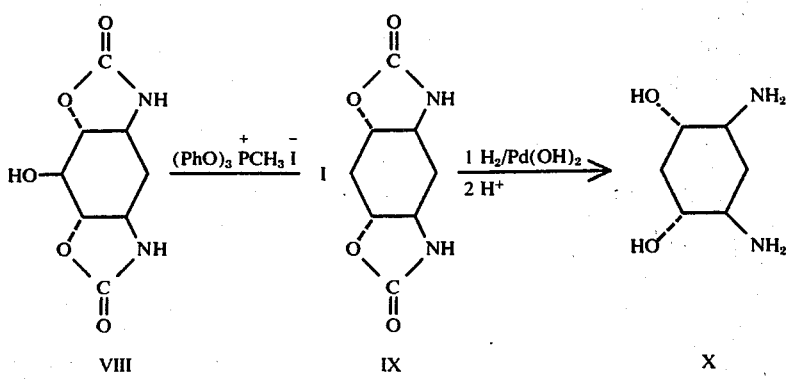

By analogy, treatment of the dicarbamate of 2deoxystreptamine (VIII) with alkylating agents such as methyl iodide under the usual conditions yields the 5-0-methyl derivative (XI). Hydrolysis of this intermediate under mild conditions affords the 5-alkoxy-analog of 2-deoxystreptamine (XII).

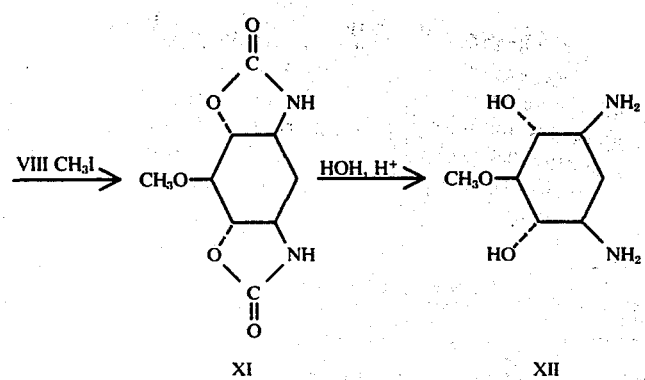

By cleaving an N,N-diacyl derivative of 2-deoxystreptamine (XIII) with periodate, a 1,3-dialdehyde (XIV) is produced. Treatment of the dialdehyde with nitromethane under alkaline conditions effects ring closure and the insertion of a nitro group at the 5-position (XV). Reduction of the nitro group to an amino group followed by hydrolysis of the N,N-diacyl functions to the free amine affords the 5-amino analog (XVI) of 2-deoxystreptamine (1,3,5-triaminocyclohexane-4,6-diol).

Anal. Calculated: $C_6H_{15}N_3O_2$; C = 44.70%; H = 9.38% Found: C = 44.84%; H = 9.32%.

2-Deoxy-5-epistreptamine may be prepared from compound XVII which may be prepared by the method

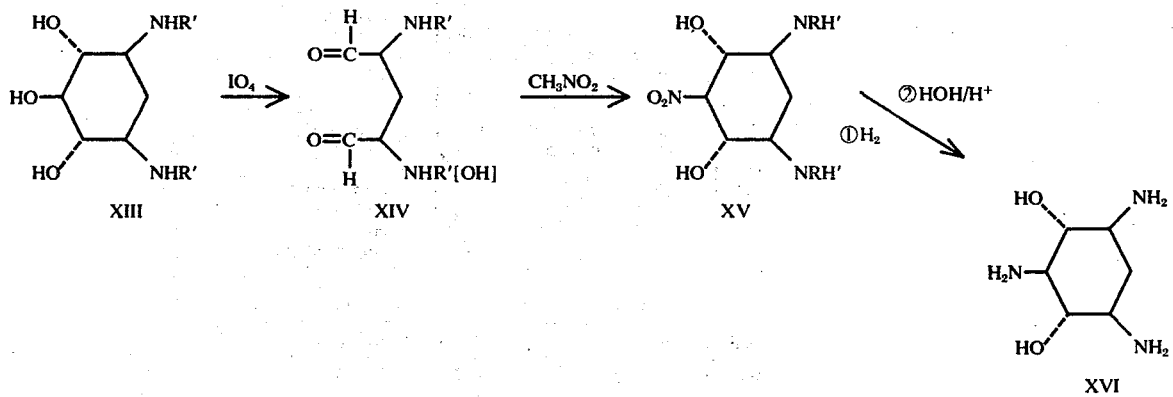

Other aminocyclitol precursors suitable for utilization in this invention may be prepared as described below:

2-Epi-streptamine (see mutamicin 4) may be prepared by the method described by Tetsue Suami et al. in the Journal of Organic Chemistry 33, No. 7, 2831–2834 (1968).

PREPARATION 1

2-Deoxy-myoinosa-1,3,5-triamine

Treat 13.0 g. of (1,3/2,4,6)-4,6-diacetamido-2-aminocyclohexane-1,3-diol with 100 ml. of 6N hydrochloric acid at reflux for 18 hours. Cool the reaction mixture to room temperature (20° C) and treat with Amberlite IRA-401S (OH form) until alkaline. Filter and evaporate the alkaline solution to obtain 7.0 g. of the title product, m.p. 192° – 194° C (dec.).

of Hasagawa and Sable Tetrahedron, 25, 35 67 (1969) the ultimate step in the sequence being the following:

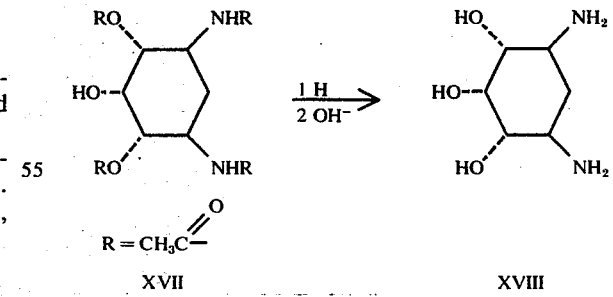

PREPARATION 2

2-Deoxy-5-epistreptamine

Treat 0.8 g. of compound XVII with 12 ml. of 6N hydrochloric acid at reflux for 3 hours. Cool the solution to room temperature (20° C) and treat with Amberlite IRA-401S (OH form) until alkaline. Filter and evaporate to a residue and chromatograph on silica gel using the lower phase of a chloroform:methanol: conc.

ammonium hydroxide (1:1:1) solvent system as eluent. The fractions containing the major component are collected and evaporated to afford the title compound (XVIII) as a white amorphous solid.

Mass spectrum: m/e = 163 (M+1)⁺. NMR: triplet $\delta 4.14$ ppm (J = 2.5 Hz, 1H, H-5 eq). $\delta 3.8 - 2.85$ ppm, 4H, multiplets. $\delta 2.34$ ppm, 1H, doublet of triplets J = 3.5, 12Hz, H-2 eq. $\delta 1.53$ ppm, 1H, quartet, J = 12Hz, H-2ax.

PHYSICOCHEMICAL DATA

The structures of the mutamicins were determined by conventional chemical analyses. Data relating to the mass spectra of compounds are set forth below, structural assignments based thereon are in accordance with the publication by Daniels, P. J. L. et al. in *Chemical Communications* No. 24, 1629–31 (1971).

Table 5

| | Mass Spectral Data | | |
|---|---|---|---|
| Mutamicin 1 | | Mutamicin 2 | |
| Peaks at (M/e) | Assignment | Peaks at (M/e) | Assignment |
| 464 | (M + 1)⁺ | 432 | (M + 1)⁺ |
| 446 | (M—NH₃)⁺ | 431 | M⁺ |
| 378 | $\begin{bmatrix} CH_2NH_2 \\ | \\ M-C=O \\ | \\ HC=CH_2 \end{bmatrix}^+$ | 414 | [M—NH₃]⁺ |
| | | 346 | $\begin{bmatrix} CH_2NH_2 \\ | \\ M-C=O \\ | \\ C=CH_2 \end{bmatrix}^+$ |
| 366, 348, 338, 320 | disaccharide ion series | 336, 316, 306, 288 | disaccharide ion series |
| 333, 315 | disaccharide ion series | 301, 283, 274, 255 | disaccharide ion series |
| 207, 189, 179, 161 | streptamine ion series | 175, 157, 147, 129 | 2,5-dideoxy-streptamine ion series |
| 127 | unsaturated monosaccharide | | |
| 160, 142, 118 | garosamine ion series | 160, 142, 118 | garosamine ion series |
| | | 127 | unsaturated monosaccharide |

| Mutamicin 4 | | Mutamicin 5 | | Mutamicin 6 | |
|---|---|---|---|---|---|
| Peaks at | Assignment | Peaks at | Assignment | Peaks at | Assignment |
| 464 | (M + 1)⁺ | 447 | (M + 1)⁺ | 448 | (M + 1)⁺ |
| 446 | (M—NH₃)⁺ | 446 | M⁺ | 447 | M⁺ |
| 378 | $\begin{bmatrix} CH_2NH_2 \\ | \\ M-C=O \\ | \\ C= \end{bmatrix}^+$ | 349, 331, 321, 303 | disaccharide ion series | 350, 332, 322, 304 | disaccharide ion series |
| 366, 348, 338, 320 | disaccharide ion series | 316, 288, 270 | disaccharide ion series | 317, 299, 289, 271 | disaccharide ion series |
| 333, 315 | disaccharide ion series | 190, 162, 144 | triamino dihydroxy cyclohexane ions | 160, 142, 118 | garosamine ion series |
| 207, 189, 179, 161, 160, 142, 118 | disaccharide ion series / garosamine ion series | 160, 142, 118, 127 | garosamine ion series / unsaturated monosaccharide | 127 | unsaturated monosaccharide |
| 127 | unsaturated monosaccharide | | | 191, 173, 163, 145 | 5-epi-2-deoxy-streptamine ion series |

(M/e) = mass to charge ratio

CHROMATOGRAPHIC DATA

The mutamicins may be distinguished from sisomicin and from each other by chromatographic techniques known in the art. For example, when chromatographed on Whatman No. 1 paper in the lower phase of a solvent system consisting of chloroform, methanol and 17% ammonium hydroxide (2:1:1) for four (4) hours the following pattern is observed:

| Rt (4 hours) | |
|---|---|
| Sisomicin | = 0.23 |
| Mutamicin 1 | = 0.11 |
| Mutamicin 2 | = 0.35 |
| Mutamicin 4 | = 0.15 |
| Mutamicin 5 | = 0.22 |
| Mutamicin 6 | = 0.08 |

Using sisomicin as reference, the mutamicins have the following R sisomicin values.

| Sisomicin | = 1.0 |
|---|---|
| Mutamicin 1 | = 0.48 |
| Mutamicin 2 | = 1.52 |
| Mutamicin 4 | = 0.65 |
| Mutamicin 5 | = 0.95 |
| Mutamicin 6 | = 0.35 |

EXAMPLE 1

Fermentation of *Micromonospora Inyoensis* Strain 1550F-1G NRRL 5742 Inoculum Preparation Inoculum Stage 1:

Under aseptic conditions, add a lyophilized culture (or cells obtained from a slant culture) of *M. inyoensis* strain 1550F-1G to a 300 ml. shake flask containing 100 ml. of the following sterile medium:
Beef extract 3 g.
Tryptose 5 g.
Yeast extract 5 g.
Dextrose 1 g.
Starch 24 g.
Calcium carbonate 2 g.
Tap water 1000 ml.

Incubate the flask and its contents for 2–5 days at 35° C. on a rotary shaker (280 r.p.m., 2 inch stroke).

Inoculum Stage 2:

Aseptically transfer 25 ml. of the fermentation medium of germination stage 1 to a two-liter shake flask containing 500 ml. of the aforedescribed sterile germination medium. Incubate the flask and its contents for three days at 28° C. on a rotary shaker (280 r.p.m., 2 inch stroke).

Fermentation Stage:

Aseptically transfer 500 ml. of the inoculum obtained from germination stage 2 to a 14 l. fermentation tank containing 9.5 l of the following sterile medium:

Dextrin 50 g.
Dextrose 5 g.
Soybean meal 35 g.
Calcium carbonate 7 g.
Cobalt chloride $10^{-6}$ molar
Tap water 1000 ml.
Antifoam (GE 60) 10 ml. Prior to sterilizing the aforedescribed medium, adjust the pH to 8 and add an aqueous solution containing 8.0 gms. of streptamine. Ferment the contents under aerobic conditions for 48–240 hours, with stirring at 250 r.p.m., with air input at 4.5 liters per l./minute and at 25 lbs. p.s.i.g. The pH of the fermentation medium changes slightly during the antibiotic production, varying in the range of about 6.8 to about 7.3.

Monitor the antibiotic production using the assay procedure described for sisomicin and when peak production is attained, harvest the product (the fermentation is usually complete in about 7 days).

Peak production for mutamicins 1, 2, 4, 5, and 6 is in the order of magnitude of from about 5 to about 50 mcg/ml.

EXAMPLE 2

Isolation of Mutamicin 1

Add 7.0 g. of oxalic acid to the whole broth from Example 1 with stirring. Acidify the broth to pH 2.0 using 6N sulfuric acid. Stir the mixture for about 15 minutes and filter using a suitable filter aid. Neutralize (pH 7.0) the filtrate with 6N ammonium hydroxide. Pass the filtrate through a 1.0 liter cation exchange resin column in the ammonium form (e.g., Amberlite IRC-50, Rohm and Haas, Philadelphia, Pa.). Discard the spent broth and elute the column with 2N ammonium hydroxide collecting fractions of about 100 ml. Monitor the column eluate by disc testing each fraction against *Staphylococcus aureus* ATCC 6538P. Combine the active fractions and evaporate to about 100 ml. in vacuo and lyophilize to obtain a solid product. Triturate the product several times with warm methanol, filter and evaporate the filtrate to a residue. Chromatograph the product on silica gel (25 g.) using the lower phase of a chloroform methanol concentrated ammonium hydroxide (1:1:1) system as the eluant. Combine and evaporate the fractions containing antibiotic activity to obtain thereby mutamicin 1.

In a similar manner, by substituting an equivalent quantity of 2,5-dideoxystreptamine, 2-epi-streptamine, 1,3,5-triaminocyclohexene-1,6-diol or 5-epi-2-deoxystreptamine, and by following the procedures of Example 1 and 2, mutamicins 2, 4, 5, and 6, respectively, may be produced.

TABLE 6

Disc Test Results (Replicate Tests) With The Mutamicins, Sisomicin and Gentamicin
Bauer-Kirby Technique[1] With 10 Mcg. Discs
Zone Size (mm)

| Organism | Mutamicin 1 | Mutamicin 2 | Mutamicin 4 | Mutamicin 5 | Sisomicin | Gentamicin |
|---|---|---|---|---|---|---|
| *Escherichia coli* | | | | | | |
| 589 | 29 | 24 | 26 | 18 | 24 | 23 |
| W677/R55 | 30 | 21 | 13 | 10 | 15 | 13 |
| LA290/R55 | 29 | 21 | 16 | ± | 13 | 12 |
| JR88 | 11 | 22 | 16 | 0 | 11 | 11 |
| JR90 | 0 | 25 | 22 | 0 | 0 | 0 |
| Swidinsky 4195 | 28 | 25 | 17 | 0 | 24 | 23 |
| ATCC 10536 | 31 | 28 | 27 | 24 | 28 | 28 |
| Baker 2 | — | — | 24 | — | — | — |
| St. Michael 1574-1 | — | 27 | 25 | 22 | — | — |

TABLE 6-continued

Disc Test Results (Replicate Tests) With The Mutamicins, Sisomicin and Gentamicin
Bauer-Kirby Technique[1] With 10 Mcg. Discs
Zone Size (mm)

| Organism | Mutamicin 1 | Mutamicin 2 | Mutamicin 4 | Mutamicin 5 | Sisomicin | Gentamicin |
|---|---|---|---|---|---|---|
| JR66 | — | 26 | 18 | 0 | — | — |
| *Pseudomonas aeruginosa* | | | | | | |
| Stone 20 | 31 | 33 | 28 | 16 | 27 | 27 |
| Stone 39 | 29 | 27 | 20 | 12 | 25 | 25 |
| Stone 130 | 14 | 25 | 14 | 0 | 14 | 12 |
| Stone 138 | 15 | 23 | 11 | 0 | 10 | 10 |
| St. Michael 762 | 24 | 26 | 19 | ± | 25 | 24 |
| St. Michael 1262 | 18 | 27 | 19 | 10 | 26 | 25 |
| St. Michael 1395 | 29 | 28 | 19 | 0 | 26 | 26 |
| St. Michael 413 | 27 | 27 | 19 | 11 | 26 | 26 |
| St. Michael 836 | — | 28 | 19 | 10 | — | — |
| D-2 | 21 | 26 | 17 | 0 | 24 | 23 |
| Capetown 18 | 19 | 22 | 16 | 0 | 14 | 12 |
| *Salmonella typhimurium* | | | | | | |
| Group B | — | 27 | 25 | 22 | — | — |
| *Klebsiella pneumoniae* | | | | | | |
| Ad 17 | 24 | 23 | 25 | 20 | 22 | 22 |
| Ad 18 | 26 | 25 | 24 | 21 | 23 | 25 |
| Ad 22 | — | — | 26 | — | — | — |
| Georgetown 3694 | 26 | 22 | 19 | 0 | 14 | 13 |
| Georgetown 3020 | 26 | 21 | 19 | 0 | 13 | 11 |
| Providence 164 | 15 | 25 | 0 | 9 | 13 | 11 |
| *Staphylococcus aureus* | | | | | | |
| ATCC 6538P | 26 | 27 | 24 | 21 | 25 | 25 |
| Wood | 28 | 29 | 26 | 25 | 29 | 27 |
| Ziegler | 25 | 28 | 24 | 23 | 26 | 26 |
| 59N | 26 | 29 | 26 | 23 | 28 | 28 |
| 1118 | — | 14 | 14 | ± | — | — |
| Grey | — | 16 | 13 | ± | — | — |
| *Streptococcus pyogenes* | | | | | | |
| C | 13 | 15 | 12 | ± | 13 | 13 |
| B-Cruz | 17 | 17 | — | — | 15 | 16 |
| 27 | — | — | 12 | ± | — | — |
| *Bacillus subtilis* | | | | | | |
| ATCC 6633 | 31 | 33 | 29 | 28 | 31 | 31 |
| *Proteus airabilis* | | | | | | |
| Harding | — | 26 | 21 | 19 | — | — |
| *Proteus rettgeri* | — | 24 | 14 | 13 | — | — |

[1]Bauer, Kirby, Sherris and Turck, American Journal of Clinical Pathology, Vol. 45, Pages 493–496 (1966)

Table 7

In vitro Activity of the Mutamicins and Sisomicin
MIC's in Mueller-Hinton Broth pH 7.2
MIC (mcg/ml)

| Organism | Mutamicin 1 | Sisomicin |
|---|---|---|
| *Staphylococcus aureus* | | |
| ATCC 6538P | 0.3 | 0.08 |
| Wood | 0.08 | 0.03 |
| Ziegler | 0.08 | 0.08 |
| 59N | 0.3 | 0.03 |
| 1118 | 3.0 | 3.0 |
| Grey | 3.0 | 3.0 |
| *Streptococcus pyogenes* | | |
| C | 3.0 | 3.0 |
| 27 | 7.5 | 3.0 |
| Cruz | 3.0 | 3.0 |
| Alvarez | 7.5 | 3.0 |
| Labay | 7.5 | 3.0 |
| Karipeds | 3.0 | 0.8 |
| *Bacillus subtilis* | | |
| ATCC 6633 | 0.03 | 0.03 |
| *Escherichia coli* | | |
| ATCC 10536 | 0.3 | 0.08 |
| Genta. adenyl W677/R55 | 0.8 | 7.5 |
| Kana. phosphor. 589 | 3.0 | 0.8 |
| Kana. phosphor. C-13 | 3.0 | 0.3 |
| Baker 2 | 3.0 | 0.3 |
| FI4-Bk | 3.0 | 0.3 |
| Genta. adenyl LA290-R55 | 3.0 | 17.5 |
| Tobra. R 4195 | 3.0 | 0.8 |
| *Klebsiella pneumoniae* | | |
| Ad 18 | 0.3 | 0.08 |
| Kana. phos. Ad 22 | 0.3 | 0.3 |
| Genta. adenyl 3694 | 0.3 | 7.5 |
| Genta. adenyl 3020 | 0.3 | 7.5 |
| Genta. adenyl 121 | 3.0 | 0.08 |
| *Pseudomonas aeruginosa* | | |
| 1262 | 3.0 | 0.8 |
| 762 | 3.0 | 0.3 |
| 1395 | 3.0 | 0.08 |
| NRRL B3223 | 0.3 | 0.08 |
| D-2 | 0.8 | 0.08 |
| Genta.-Tobra.-R. Travers | >25 | >25 |
| Genta. acetyl Stone 130 | 17.5 | 17.5 |
| Stone 138 | 17.5 | 7.5 |
| Stone 20 | 3.0 | 0.3 |
| Stone 39 | 3.0 | 0.8 |
| Genta. acetyl Capetown 18 | 7.5 | 7.5 |
| *Proteus rettgeri* | 3.0 | 0.8 |
| Providence (Genta. R.) 164 | >25 | >25 |
| *Salmonella typhimurium* B | 3.0 | 0.3 |
| *Serratia* 127 | 0.8 | 0.8 |
| *Candida albicans* | >25 | >25 |
| *Trichophyton rubrum* | >10 | >25 |
| *Aspergillus niger* | >10 | >25 |

Table 8

In vivo Activity of the Mutamicin 1 and Sisomicin
Protection Tests in Mice
PD$_{50}$ (mg/kg)

| Organism | Mutamicin 1 | Sisomicin |
|---|---|---|
| *Staphylococcus* | | |
| Gray | 6.0 | 1.8 |
| *Escherichia coli* | | |
| Sc. | 5.0 | 1.7 |
| 6922 | 2.5 | 2.0 |
| *Pseudomonas aeruginosa* | | |
| 2552 | 15.3 | 2.8 |
| 2557 | 17.1 | 2.7 |
| Sc. | 2.5 | 1.1 |

Acute Toxicity

| Route | | LD$_{50}$ (mg/kg) |
|---|---|---|
| I.V. | | 110    34 |

Table 8-continued

| In vivo Activity of the Mutamicin 1 and Sisomicin Protection Tests in Mice PD₅₀ (mg/kg) | | |
|---|---|---|
| Organism | Mutamicin 1 | Sisomicin |
| I.P. | >700 | 190 |

The mutamicins are broad spectrum antibacterial agents which may be used for in vitro or in vivo application. For in vitro application, the mutamicins may be combined with detergents and used to clean and disinfect the surfaces of laboratory equipment such as tables, scales, cages and the like. For in vivo application, the compounds may be used to treat animals, especially warm blooded animals, having bacterial infections. They are of particular value for treating infections caused by bacteria resistant to aminoglycoside antibiotics used heretofore.

In many instances, bacterial resistance is related to the organism's ability to inactivate the antibacterial agent via enzymatic (biochemical) means. Some species inactivate aminoglycosides antibiotics by acetylating the antibacterial agent, others by phosphorylation and still others by adenylylating. Some strains have several different inactivating capabilities. Further, the inactivation reactions occur at a specific site or sites on the antibacterial agent. We have shown by the compounds of this invention that alteration of sites on the antibiotic molecule not directly involved in inactivation processes can nevertheless frustrate these inactivation processes. The tables evidencing the activity of the mutamicins include many strains of bacteria exhibiting such resistance. The tables illustrate that the mutamicins include compounds which are active against strains having different mechanisms of inactivation of gentamicin, sisomicin, kanamycin, neomycin and torbramycin. For example, some mutamicins are effective against strains of *E. coli* which contain adenylylating R factors such as E. coli W677/R55 and LA290/R55. These *E. coli* strains are resistant to gentamicin, sisomicin and torbramycin. Some are also effective against gentamicin, tobramycin and kanamycin resistant adenylylating strains of *Klebsiella pneumoniae* and also kanamycin, neomycin phosphorylating strains of *E. coli* and *Klebsiella pneumoniae*. Further, some mutamicins are effective against gentamicin and sisomicin resistant strains of *Pseudomonas aeruginosa* and gentamicin, sisomicin, tobramycin resistant Providence which is sensitive to kanamycin. Thus, the mutamicins afford a means for combatting strains of bacteria which have already developed a variety of mechanisms for resisting the action of many of the antibiotics known in the art or currently in commercial use.

We claim:

1. A compound selected from the group consisting of compounds of the formula:

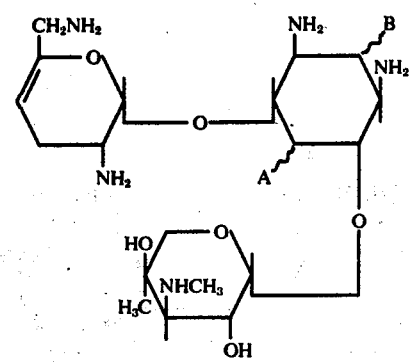

and the non-toxic acid addition salts thereof wherein A is a member selected from the group consisting of hydrogen, amino, hydroxy and ($C_1$–$C_8$) alkoxy, B is a member selected from the group consisting of hydrogen, and hydroxy, wherein the wavy lines connecting A and B to the ring nucleus denotes that such groups may be in any of the possible, stereoisomeric forms, with the proviso that when B is hydrogen and A is hydroxyl, A must be cis to the glycosyl groups adjacent thereto and the further proviso that when A is amino, it must be trans to the glycosyl groups adjacent thereto.

2. The compound of claim 1, wherein A is hydroxy, said A being cis to the glycosyl groups adjacent thereto, and B is hydrogen, said compound being mutamicin 6.

3. The compound of the formula:

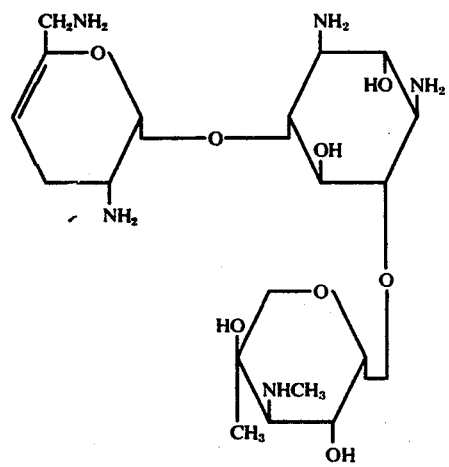

the compound being mutamicin 1.

4. The compound of the formula:

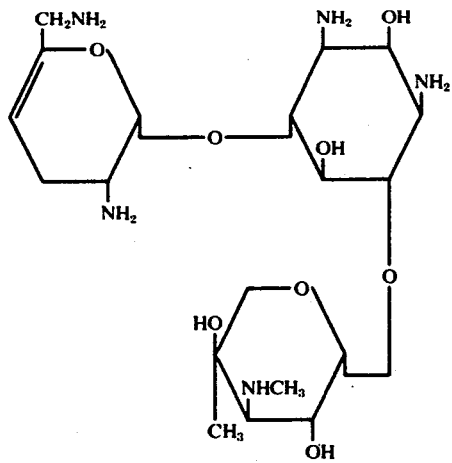
the compound being mutamicin 4.
5. The compound of the formula:
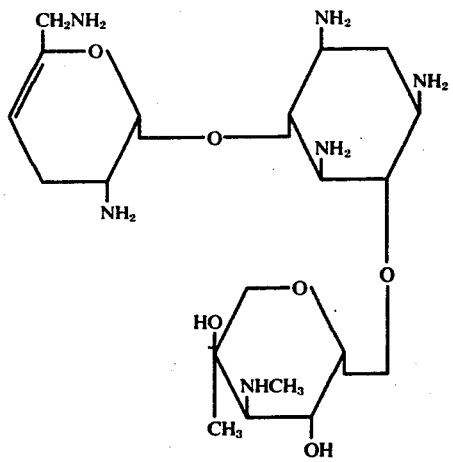
the compound being mutamicin 5.
6. The compound of the formula:
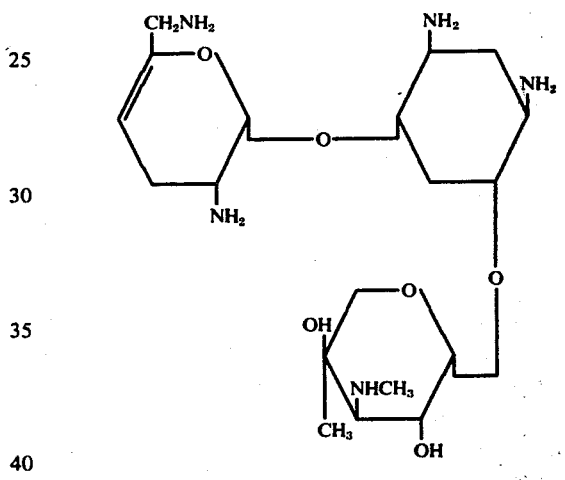
the compound being mutamicin 2.

UNITED STATES PATENT OFFICE
CERTIFICATE OF CORRECTION

Patent No. 4,011,390     Dated March 8, 1977

Inventor(s) Marvin J. Weinstein et al.

It is certified that error appears in the above-identified patent and that said Letters Patent are hereby corrected as shown below:

On the Title Page, assignee should read

-- [73] Assignee: Schering Corporation,

Bloomfield, N. J. --.

*Signed and Sealed this*

*First* Day of *November 1977*

[SEAL]

Attest:

RUTH C. MASON
*Attesting Officer*

LUTRELLE F. PARKER
*Acting Commissioner of Patents and Trademarks*